Oct. 1, 1968 R. B. GRIFFITH Plant Pat. 2,835
APPLE TREE
Filed March 13, 1967
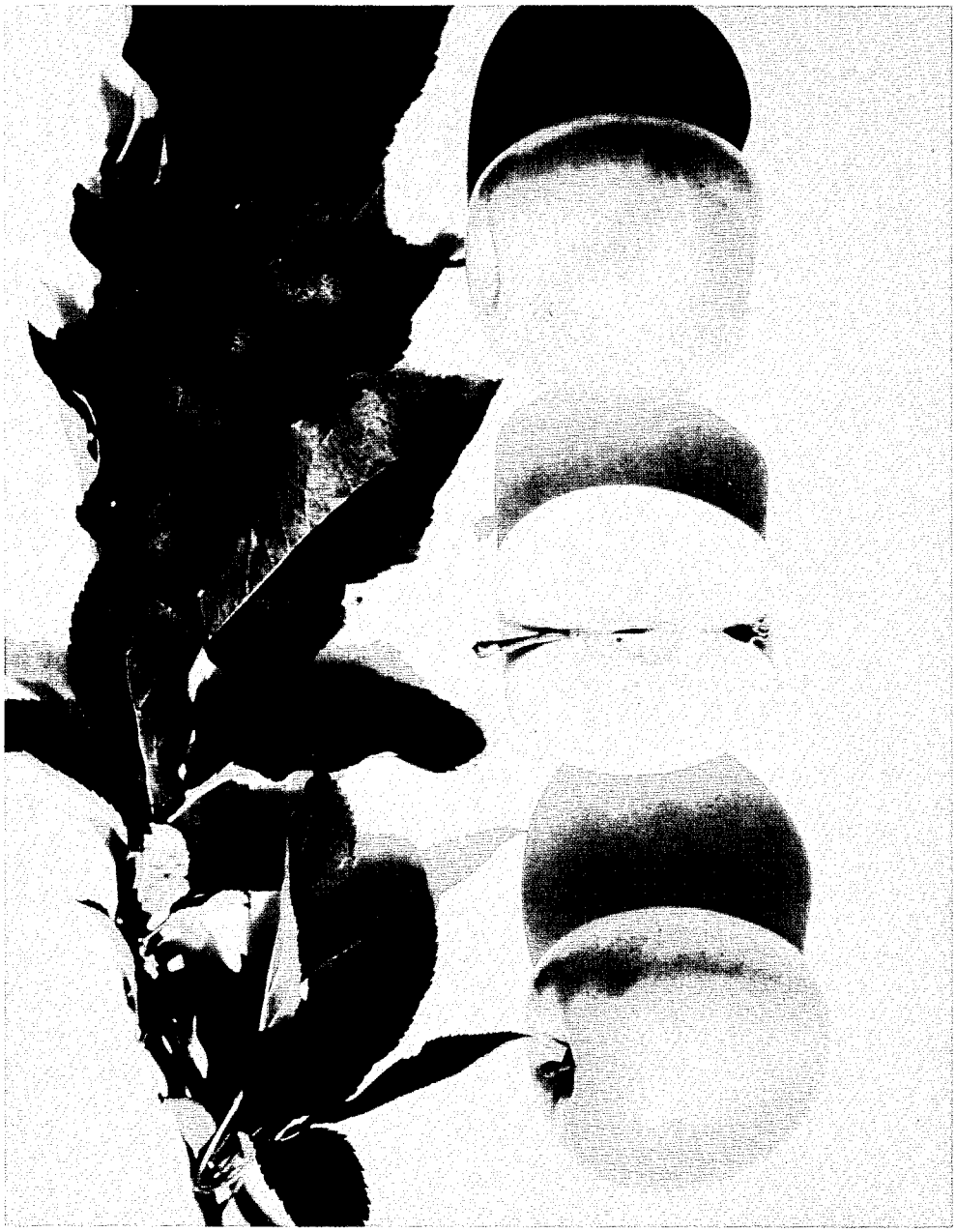
Inventor.
Ralph B. Griffith
By: Robb & Robb
Attorneys.

United States Patent Office

Plant Pat. 2,835
Patented Oct. 1, 1968

2,835
APPLE TREE

Ralph B. Griffith, Cobden, Ill., assignor to Stark Bro's Nurseries & Orchards Company, Louisiana, Mo., a corporation of Missouri

Filed Mar. 13, 1967, Ser. No. 622,829
1 Claim. (Cl. Plt.—34)

The present invention relates to a new and distinct variety of apple tree which was discovered by me in my cultivated orchard in Union County, Ill. as a newly found seedling of unknown parentage.

Prior to my discovery, I had purchased from a local nursery and planted in my orchard some apple trees which were represented to me as being the variety known as "Rome Beauty" (unpatented). The new seedling grew as a sprout from the seedling root stock of one of these trees, and my attention was attracted thereto by the fact that the fruit borne thereby was quite different from the fruit of "Rome Beauty," and instead, resembled in shape, size and flavor the fruit of the variety known as "Golden Delicious" (unpatented). However, the fruit of the new seedling developed a yellow ground color earlier than the fruit of "Golden Delicious," and acquired an attractive and distinctive pink to red blush. Further observations of the new seedling, and of progeny thereof derived by grafting, as performed on my behalf in my nursery in Union County, Ill. and at Louisiana, Mo., have convinced me, as well as other experienced apple growers and expert pomologists that my new seedling represents a new and improved variety which is distinguished from all other previously known apple varieties, as evidenced by the following unique combination of characteristics which are outstanding in the new variety:

(1) A general resemblance of the fruit in shape, size and flavor to the fruit of "Golden Delicious," but which develops an earlier yellow ground color and acquires a distinctive and attractive pink to red blush;

(2) A later fruit maturity of about 10 days later than the fruit of "Golden Delicious";

(3) A longer keeping quality of the fruit;

(4) A waxy appearance of the fruit skin which does not develop russet, and absence of any tendency of the fruit to shrivel in normal storage as does the fruit of "Golden Delicious";

(5) Good resistance to spray injury; and (6) A richer and more acid flavor of the fruit than the fruit of "Golden Delicious."

The accompanying drawing shows typical specimens of the foliage and fruit of my new variety, as well as a typical branch section illustrating the semi-spur type of fruiting growth, with one of the fruit specimens shown in longitudinal cross-section, all as depicted in color as nearly true as it is reasonably possible to make the same in a color illustration of this character.

The following is a detailed description of my new variety, with color terminology in accordance with Ridgway's Color Standards and Nomenclature, hereinafter abbreviated as (Ridgway), Horticultural Colour Guide, hereinafter abbreviated as (HCG), and Munsell Color Chart, hereinafter abbreviated as (Munsell), except where general color terms of ordinary dictionary significance are obvious:

Location where grown and observed: Union County, Ill.

Dates of first and last pickings: September 29 and October 3, respectively.

Tree: Medium large size; vigorous; spreading; low; round-topped; rapid growing; hardy; productive; regular bearer.

*Trunk.*—Medium stockiness; smooth.

*Branches.*—Medium thickness; smooth; much-branched. Color—Olive Brown, Plate XL, Color No. 17‴, tone M (Ridgway).

*Lenticels.*—Numerous; small.

*Leaves.*—Medium large size; medium narrow; medium length; ovate; taper-pointed; medium thickness; slightly rugose. Average length—from 4¼ inches to 4½ inches. Average width—from 2⅛ inches to 2¼ inches. Color—Spinach Green, Plate 0960/1, page 187, volume 2 (HCG). Margin—coarsely serrate. Petiole—medium length; medium slenderness; length—from 1⅛ inches to 1¼ inches.

Fruit:

*Maturity when described.*—Hard ripe.

*Size.*—Uniform. Axial diameter—3 inches. Transverse diameter—2⅞ inches.

*Form.*—Truncate at base; oval.

*Cavity.*—Symmetrical; rounded at base; acute; undulate; pubescent toward apex. Depth—¾ inch. Breadth—1 inch. Markings—russeted; color—Tawny Olive, Plate XXXIX, Color No. 17″, tone *i* (Ridgway).

*Basin.*—Symmetrical; wide flaring base, undulate; glabrous. Depth—5/16 inch. Breadth—⅞ inch. Markings—none.

*Stem.*—Clubbed; medium slender; pubescent. Length—from ¾ to 1 inch. Breadth— 1/16 inch. Markings—russetted.

*Calyx.*—Closed; segments persistent; narrowly lanceolate; acute; about ¼ inch long; approximate; converged from base toward center; pubescent on both inner and outer surfaces.

*Skin.*—Thick; tough; glossy; waxed. Dots—obscure; many; small; even; ruptured; circular; color—Indian Yellow, Plate 6/3, page 6, volume 1 (HCG); distribution—uniform, except few near basin and cavity. Ground color—Vivid Greenish-Yellow, Plate 7.5Y 8/12 (Munsell). Color markings—blushed; bright; color—Scarlet Red, Plate I, Color No. 5 (Ridgway). Bloom—wanting. Scarfskin—wanting. General color effect—yellow with pink blush.

*Flesh.*—Juicy. Color—satiny white with yellowish tint. Texture—firm; fine; crisp. Flavor—subacid; rich. Aroma—distinct. Quality—best.

*Core.*—Median. Bundle area—small; narrowly ovate; symmetrical at base; acute at base. Halves of core—equal. Bundles—inconspicuous; color—yellowish tinged. Core lines—clasping; indistinct in cross section. Carpellary area—indistinct; small. Calyx tube—glabrous toward base; apex narrowly cone-shaped; entire depth—⅝ inch. Styles—present; united toward base; pubescent toward base. Stamens—in one basal whorl. Seed cells—axile; closed; cell walls—distant; thin; tough; length—¾ inch; breadth—5/16 inch. Longitudinal section—orbicular, obtuse at apex. Cross section—broad. Surface—fissured; tufted.

Seeds:

*Average number.*—5 or 6 perfect, and 2 or 3 imperfect; 2 per cell.

*Length.*—3/8 inch.

*Breadth.*—3/16 inch.

*Form.*—Obtuse.

*Color.*—Chocolate, Plate XXVIII, Color No. 7″, tone M (Ridgway).

Keeping quality: Good; about 210 days in ordinary storage.

I claim:

1. A new and distinct variety of apple tree, substantially as herein shown and described, characterized particularly as to novelty by the unique combination of a general resemblance of the fruit in shape, size and flavor to the fruit of "Golden Delicious," but which develops an earlier yellow ground color and acquires a distinctive and attractive pink to red blush, a later fruit maturity of about 10 days later than the fruit of "Golden Delicious," a longer keeping quality of the fruit, a waxy appearance of the fruit skin which does not develop russet, and absence of any tendency of the fruit to shrivel in normal storage as does the fruit of "Golden Delicious," good resistance to spray injury and a richer and more acid flavor of the fruit than the fruit of "Golden Delicious."

No references cited.

ROBERT E. BAGWILL, *Primary Examiner.*